United States Patent [19]

Hoyer et al.

[11] 3,950,854
[45] Apr. 20, 1976

[54] METHOD AND APPARATUS FOR MEASURING AREA UNDER A CURVE

[75] Inventors: Karl Hoyer, Leinfelden; Heinrich Stöckle, Hemmingen, both of Germany

[73] Assignee: Robert Bosch G.m.b.H., Stuttgart, Germany

[22] Filed: Nov. 20, 1974

[21] Appl. No.: 525,490

[30] Foreign Application Priority Data

Dec. 8, 1973 Germany............................ 2351334

[52] U.S. Cl............................ 33/123; 235/61.6 A; 324/61 R
[51] Int. Cl.²................................................ G01B 7/32
[58] Field of Search....................... 33/121, 123, 15; 235/61.6 A, 61.6 B; 324/61 R; 356/203

[56] References Cited
UNITED STATES PATENTS

| 912,181 | 2/1909 | Schattner | 346/76 R |
|---|---|---|---|
| 1,580,112 | 4/1926 | Bone | 340/200 |
| 2,680,838 | 6/1954 | Harnisch | 33/123 |
| 3,308,376 | 3/1967 | Katz | 324/61 |
| 3,491,344 | 1/1970 | Ferber | 346/135 |
| 3,534,382 | 10/1970 | Hurst | 346/135 |
| 3,614,241 | 10/1971 | Sanford | 356/203 |
| 3,623,812 | 11/1971 | Hannig | 356/203 |
| 3,767,899 | 10/1973 | Barter | 346/146 |

FOREIGN PATENTS OR APPLICATIONS 276,449 5/1971 U.S.S.R................................. 33/123

Primary Examiner—Richard E. Aegerter
Assistant Examiner—John W. Shepperd
Attorney, Agent, or Firm—William R. Woodward

[57] ABSTRACT

An electrically operated recording measuring instrument burns out the trace of a curve on a moving record medium coated on both sides with an evaporated metal layer. The power supply for the burnout current also feeds an auxiliary writing member for burning out an additional trace to isolate an area of the metal layer under the curve and, if desired, to subdivide the area in a similar way. The power supply also furnishes a higher voltage to a test probe for burning out any remaining conducting bridges across the burnout traces before capacitance measurements are made which can read directly in terms of area or relative area. The method and apparatus are particularly usable for photoelectrically evaluating blood samples treated by electrophoresis to separate the proteins.

5 Claims, 3 Drawing Figures

METHOD AND APPARATUS FOR MEASURING AREA UNDER A CURVE

This invention relates to method and apparatus for measuring areas between a curve and a base line, particularly where the curve in question is traced out by a recording measuring instrument. The method and apparatus of this invention are particularly useful to evaluate blood analysis curves resulting from photoelectric measurement of blood samples that have been subjected to electrophoresis.

In many cases it has been found necessary to integrate curves drawn by a recording instrument, that is, to measure the areas enclosed between the curve and some base line. Such a need arises particularly in the evaluation of electrophoretic blood analyses.

In electrophoretic blood analysis, a blood sample is first placed on a glass slide and subjected to an electric field causing a flow of ions which causes the lighter molecules to move more rapidly than the heavier ones, so that after a little while a separation of the various blood proteins results. Several groupings of proteins then are formed which appear, after they are made visible with a dye, as dark stripes on the slide. The sample thus treated is then moved slowly across a light beam while a photoelectric device measures the transmitted light and applies an electrical signal to the writing arm of a recording device. A recording medium, such as a paper record, is moved past the writing arm in synchronism with the movement of the sample slide, so that a characteristic curve is drawn on the paper record. On such a record each section of the curve between two minima represents one dark stripe on the slide and, hence, the relative content of one kind of blood protein. The area enclosed by each such portion of the curve between it and a reference base line, when compared to (divided by) the area enclosed between the entire curve and the base line, yields the percentage composition of the particular kind of protein. It is therefore necessary to determine the area below the curve as a whole and the constituent areas below particular portions of the curve.

Evaluation of blood analysis in the manner described has heretofore been carried by providing a second writing arm which is to be operated so as to draw the integral of the curve. The individual protein types are separated from each other by drawing perpendicular lines through the minima. The second writing arm is then manipulated according to a geometrical law to provide a graphical evaluation of the integral. This evaluation is expensive, consumes a great deal of time and places high requirements on the care that must be exercised by the operator. An automatic integrator is known that can be used for this purpose, but it is very elaborate in construction and high in cost.

It is an object of the present invention to provide an integration method requiring low expenditure of working time and material and to provide apparatus for practice of the method which is simple and cheap to produce.

SUBJECT MATTER OF THE PRESENT INVENTION

Briefly, a recording medium in the form of an insulating sheet such as paper coated on both sides with a vapor-deposited metal layer is used in a recording instrument that applies current through one of the metal layers of the recording medium as it traces the curve, in so doing burning out a narrow trace of the curve in one of the metal layers. An additional writing member is provided and supplied with current to be applied to the recording medium by which additional traces can be burned out on the recording medium to isolate electrically areas of the metal layer corresponding to the areas to be measured. The isolated areas are then measured capacitively by measuring the capacitance between the isolated areas of one metal layer and the metal layer on the other side of the recording medium.

It is particularly convenient to measure the entire area of interest under a curve first, and normalize measurement to the value of 100, so that when additional traces have been made subdividing the area under the curve, the areas thus subdivided would be measured in terms of percentage of the total area of interest.

The apparatus for the practice of the above method of measurement includes a capacitive measurement apparatus with at least one probe for connection to an isolated area of the recording medium, a power supply for supplying burnout current to the recording medium through the writing arm of a recording instrument, an auxiliary writing member for providing additional traces to define areas adjoining the curve that are to be measured and a contact probe for applying a higher potential to a traced out area to burn off bridges that may remain across the burnout traces.

The advantage of the invention lies particularly in that this method of integration is usable for any type of curve traced by a curve writer. The method delivers rapid and exact results and the apparatus for the carrying out of the method is simple and cheap to supply.

The invention is further described by way of example with reference to the accompanying drawing, in which.

Figure 1:
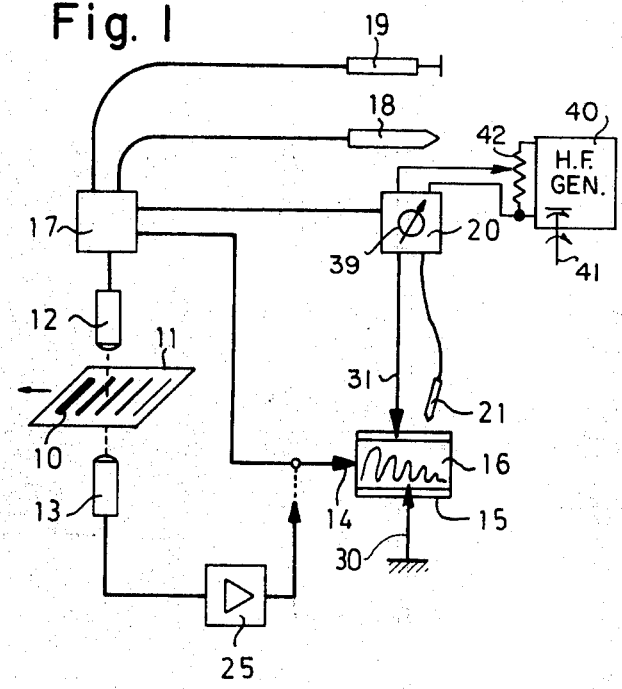
FIG. 1 is a diagram of an apparatus for the curve integration method according to the invention as used for determination of the protein distribution in blood.

The apparatus shown diagramatically in FIG. 1 applies the method of the present invention for determination of albumin and globulin in blood analysis. The previously prepared blood sample 10 carried on the slide 11 is slowly moved through the photoelectric densitometer that utilizes a light source 12 and a photoelectric detector 13. The photomultiplier 25 and its built-in amplifier serve to control the movement of the writing arm 14 of a line tracer 15. The displacement of the writing arm is the greater, the smaller is the received light intensity at the receiver 13. The recording medium 16 for the line tracer 15 is of an insulating sheet material, preferably paper, covered on both sides by a vapor-deposited metal layer, preferably of aluminum.

A power supply 17 contains two or more separate voltage sources. It is connected with the writing arm 14 of the line tracer 15, so that a current flows from the writing arm 14 to one metal layer (16a in FIG. 3) of the recording paper 16. This current burns out a trace 22 as the recording medium is moved, the trace corresponding with the curve drawn on the recording medium by the writing arm 14. In order to make the burnout trace more visible, a black pigmented film 16c is applied in the form of a lacquer, between the paper 16d and the metal layer 16a upon which the writing arm writes.

In addition, the power supply 17 also supplies electricity to an auxiliary writing member 18. This last serves for the burning out of additional lines on the recording medium necessary to isolate areas to be measured, this being preferably done manually. The power supply 17 also supplies a contact probe 19 with a greater electrical current, for example by means of a higher voltage, for the purpose of burning out conducting bridges that may possibly remain across an original burnout trace, particularly a burnout trace drawn by an automatic burning arm such as the writing arm 14.

Figure 3:
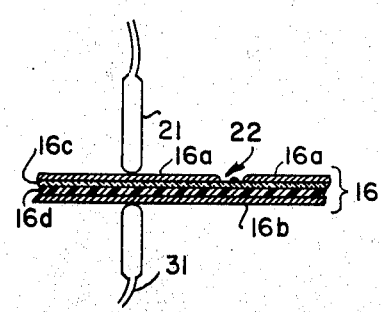
FIG. 3 is a cross section of the recording medium shown with connections for capacitance measurement.

A capacitance measuring device 20 is provided for measuring the capacitance between isolated portions of the metal layer 16a on the recording medium and the metal layer 16b on the opposite side of the medium. For this purpose, the capacitance measuring device has a measuring conductor 31 connected to the backside layer 16b of the recording medium and another measuring conductor terminating in a test probe 21 which can be brought into contact with the individual isolated portions of the metal layer defined by the burnout traces for successively measuring the capacitance thereby provided, as shown in FIG. 3. Such a capacitance measuring device may, for example, comprise a high-frequency generator 40 arranged to apply an alternating voltage on the two electrodes of the capacitance to be measured. The current flowing through the capacitor is proportional to the amplitude and the frequency of the alternating current, as well as to the capacitance of the capacitor. The indicating meter 39 included in the capacitance measuring device 20 can therefore be normalized to a particular value by variation of the frequency or of the amplitude of the alternating current, in the first case by means of the frequency control 41 and in the second case by means of the amplitude control 42.

Figure 2:
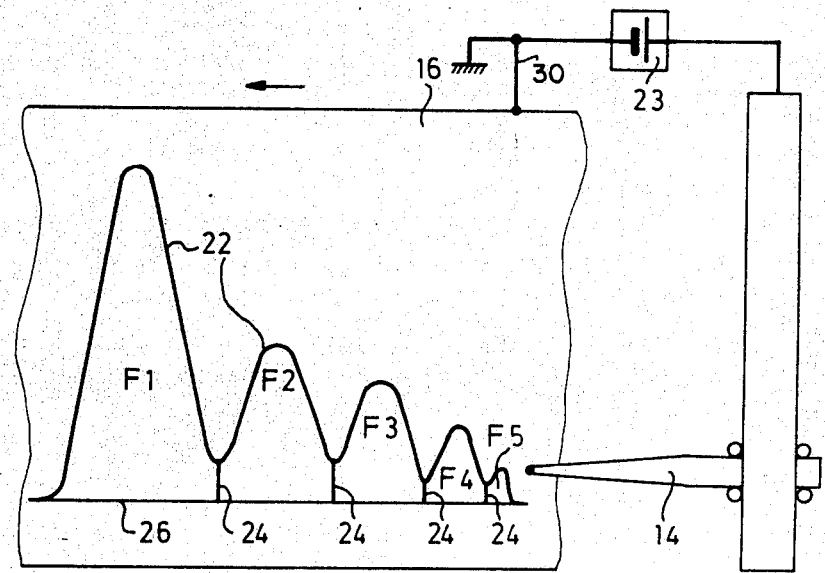
FIG. 2 is a diagram showing the curve drawn by a line tracer, as used in the invention.

The measuring method can be best explained with reference to the curve 22 by a writing arm 14 of the line tracer 15 as shown in FIG. 2. As already described, the writing arm 14 inscribes a trace 22 on one metal layer of the recording medium 16 corresponding to the course of the signal received by the detector 13. There is thus defined an aggregate surface F1 – F5 that is still open below. The burning out of the trace 22 takes place as the result of the voltage source 23 contained in the power supply 17 being applied between the recording medium 16 and the writing arm 14. Then a horizontal trace 26 is burned out with the auxiliary writing member 18 to provide a base line closing off the aggregate area F1 – F5. The contact probe 19 then brought into contact with the combined area F1 – F5 to burnout the conducting bridges still remaining in the boundary traces. A higher current thus disposes of the bridges, which are the higher resistance parts of the circuit between the probe 19 and the grounded return conductor 30.

The contact probe 21 of the capacitance measuring device 20 is then brought into contact with the isolated surface between the curve trace 22 and the line trace 26 as shown in FIG. 3 and the measured value is normalized to the value 100 in one of the ways above mentioned. Then, using the auxiliary writing member 18 again, additional straight traces are drawn from the minima of the curve perpendicular to the lower edge of the recording medium, which is of course aligned in the direction of movement of the medium and corresponds to the direction of movement of the slide 11 of FIG. 1. The additional traces 24 intersect the line 26 and divide up the previously enclosed area into individual areas F1, F2 . . . F5. Then the capacitance of the capacitors formed by each of these individual areas with the metal layer on the other side of the recording medium are measured with the capacitance measuring device 20 and because of the previous normalizing, the result can be read off directly in percentages of the total area. These measured percentages are, of course, the respective percentages of the blood protein composition represented by each of the electrophoretically separated proteins.

Comparative measurements made with a device according to the invention have shown that the accuracy of the method of the invention is substantially greater than that of the previous graphical methods. The maximum error using the above-described method and device is found to be ± 5%, contrasted with the graphical method where particularly with very small area segments, the error can go as high as 25%.

Although the invention has been described with reference to a particular illustrative example, it will be understood that variations are possible within the inventive concept.

For example, at one or both ends the base line 26, instead of directly intersecting the curve, may be drawn with perpendicularly upturned ends intersecting the curve.

We claim:

1. A method of evaluating electrophoresis results embodied in matter electrophoretically distributed on a slide, comprising the steps of:

scanning a slide bearing an electrophoretically treated distribution of matter thereon to produce an electric signal representing the density of said matter as a function of position along a line of scan;

recording said signal in the form of a curve representative of said density as a function of said position by causing said signal to produce a burnout trace (22) on a first metal layer having the characteristics of a vapor-deposited metal layer and located on a recording medium composed of an insulating web of uniform thickness having a metal layer on each of the two sides thereof, by applying electric current to said first metal layer through a writing arm (14) movable relative to said recording medium in contact therewith, and responsive to said signal for one dimension of said relative mobility, which current is sufficient to interrupt the continuity of said first metal layer by vaporization thereof at the location of contact of said writing arm with said recording medium;

tracing also a base line for said curve by burning out a substantially straight trace (26) on said recording medium representative of a reference density for material on said slide by means of a second writing arm (18) through which current is applied to said first metal layer of said recording medium, said second writing arm being positioned for its tracing operation so that the resulting base line is offset to one side of said curve, said base line being drawn, or being provided with connecting trace line(s), so as to intersect or connect with said curve trace at its end portions and thereby isolate electrically an area of said first metal layer between said curve trace and said base line;

forming an electric circuit by connecting said isolated area of said first layer with said second layer;

measuring the capacitance of said electrically isolated area with respect to the second metal layer affixed to the other side of said web of said recording medium by means of a device in said electric circuit having an indicating meter and an adjustment capable of proportionally affecting readings of said meter;

normalizing the reading of said meter by means of said adjustment so that it provides a predetermined meter reading value when measuring the capacitance of said electrically isolated area, whereby fractions of said area may be subsequently measured directly in proportional units with said device;

thereafter tracing lines (24) substantially perpendicular to said base line by means of a writing arm having the same current-applying and local burn-out effect as said first and second writing arms by moving said lastmentioned writing arm in a path on said first metal layer of said recording medium such that said perpendicular lines intersect said curve at minima of the distance between said curve and said base line and subdivide the area between said curve and said base line, and then forming an electric circuit by connecting said subdivided areas successively in circuit with said device and said second layer and measuring areas isolated by said traces in proportional units by measuring the capacitance between the metal layer portions isolated by said traces and said second metal layer by means of said device.

2. A method as defined in claim 1 in which, prior to the tracing of said perpendicular lines to subdivide the area between said curve and said base line, an additional method step is performed in which said curve trace (22) is freed of conducting bridges by applying to the portion of the metal layer between said curve trace (22) and said base line trace (26) a voltage relative to the portion of said metal layer on the other side of said curve trace which is sufficient to burn out residual conducting bridges that may be present.

3. Method as defined in claim 1 in which, in the first curve tracing step there defined, relative movement of said recording medium and said first writing arm producing said curve trace is effected by moving said recording medium in a first direction in a movement according with the scanning of said slide and moving said writing arm in a second direction substantially perpendicular to said first direction in accordance with the density of matter on said slide represented by said signal.

4. Method as defined in claim 3, in which, prior to the performance of the curve tracing step there referred to, the measurement of the density of said matter on said slide is facilitated by a preliminary step of applying a dye to the slide to provide opacity of said slide substantially proportional to the density of electrophoretically displaced matter.

5. Method as defined in claim 1, in which the step of tracing said perpendicular lines is carried out by the use of the same second writing arm previously used to trace said base line.

* * * * *